United States Patent
Sicken et al.

(10) Patent No.: US 6,600,068 B2
(45) Date of Patent: Jul. 29, 2003

(54) PROCESS FOR PREPARING ETHANEBIS (METHYLPHOSPHINIC) ACID

(75) Inventors: Martin Sicken, Köln (DE); Hans-Peter Schmitz, Brühl (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/046,107

(22) Filed: Dec. 19, 2001

(65) Prior Publication Data

US 2002/0079480 A1 Jun. 27, 2002

(30) Foreign Application Priority Data

Dec. 23, 2000 (DE) ......................... 100 65 054

(51) Int. Cl.⁷ ................................................. C07F 9/30
(52) U.S. Cl. ........................................................ 562/20
(58) Field of Search ............................... 562/8, 20, 23, 562/24

(56) References Cited

U.S. PATENT DOCUMENTS

| | | | |
|---|---|---|---|
| 2,957,931 A | * 10/1960 | Hamilton et al. | .......... 554/78 |
| 3,962,194 A | 6/1976 | Bollert et al. | |
| 4,001,352 A | * 1/1977 | Kleiner et al. | |
| 5,780,534 A | 7/1998 | Kleiner et al. | |
| 6,013,707 A | 1/2000 | Kleiner et al. | |

FOREIGN PATENT DOCUMENTS

| | | |
|---|---|---|
| DE | 2 158 765 | 5/1973 |
| DE | 2 236 037 | 2/1974 |
| DE | 2 302 523 | 8/1974 |
| EP | 0 699 708 | 3/1996 |

OTHER PUBLICATIONS

CA:118:93214 abs of Phosphorus, Sulfur and Silicon and the Related Elements by Toulhoat et al 71(1–4) pp 127–138 1992.*

Houben, Method der organisch Chemie vol. 21/1 p. 306, 1963.*

English abstract for DE 2158765, May 30, 1973.

U.S. patent application, Ser. No. 10/025,712, filed Dec. 19, 2001, Sicken, et al.

U.S. patent application, Ser. No. 10/025,739, filed Dec. 19, 2001, Sicken, et al.

S.M. Shner, et al., "Reactions of BIS–2–Chloroethyl Hydrogen Phosphite and Its Derivatives", J. Gen. Chem., USSR, 37, (1967), p. 390–392.

K. Moedritzer, et al., "Synthesis and Properties of Mono– and Poly–Methylene–Diphosphonic Acids and Esters", J. Inorg. Nucl. Chem., 1961, vol. 22, p. 297–304.

Claibourne E. Griffin, et al., "Phosphonic Acids and Esters. I. Radical Initiated Addition of Phosphorous Acid to Olefins", 24, (1959), p. 2049–2051.

Houben–Weyl, Methoden der organischen Chemie, Supplementary vol. 20, p. 14–75, 1987.

Przemyslaw Mastalerz, "Synthesis of some ethylene–(P, P'–Dialkyl)–Diphosphinic acids as new potential antimetabolites of succinic acid", Roczniki Chem., Ann. Soc. Chem. Polonorum, 38, 61, (1964), p. 61–65.

XP–002165520, Nifant'ev, E.E., et al., "Reactions of acetylenes with hypophosphorous and phosphonous acids", Journal of General Chemistry USSR, bd. 56, Nr. 4, Sep. 20, 1986, p. 680–688.

* cited by examiner

*Primary Examiner*—Jean F. Vollano
(74) *Attorney, Agent, or Firm*—Anthony A. Bisulca

(57) ABSTRACT

The invention relates to a process for preparing ethanebis (methylphosphinic) acid which comprises reacting ethyne (acetylene) with methyl phophonous acid.

The invention further relates to the use of the ethanebis(methylphosphinic) acid prepared by this process for preparing flame retardants or preparing other phosphorus-containing products.

15 Claims, No Drawings

PROCESS FOR PREPARING ETHANEBIS (METHYLPHOSPHINIC) ACID

BACKGROUND OF THE INVENTION

The present invention relates to a process for preparing ethanebis(methylphosphinic) acid from methylphosphinic acid, and also to the use of the products prepared by this process.

Phosphinic acids and salts of these may be prepared by a variety of methods, and have been described widely within the literature.

Organic phosphinic acids, and their salts and esters are known flame retardants. For example, EP 0 699 708 A1 describes flame-retardant polyester molding compositions, these being rendered flame-retardant by adding the calcium or aluminum salts of phosphinic or diphosphinic acids. The abovementioned salts are obtained by reacting the corresponding phosphonic acids with calcium hydroxide or aluminum hydroxide.

Due to their high phosphorus content and especially their bidentate nature, the diphosphinic acids are described as highly effective reactive flame retardants for polyesters, e.g. for textile applications. This particularly applies to ethanebis(methylphosphinic) acid, specifically in the form of its glycol ester (DE 22 36 037 A1).

The preparation of ethane(methylphosphinic) acid is technically very complicated, an example of the procedure being an Arbuzov reaction of diisopropyl methylphosphonous diesters with ethylene bromide [P. Mastalerz, Rocziniki Chem 38 (1964), pp. 61–64], followed by ester cleavage. The phosphonous diester used is prepared from methylphosphonous dichloride by reaction with alcohols.

Another way of preparing ethanediphosphonic acids is proposed in DE 23 02 523 A1 by reacting alkylphosphonous esters with ethyne (acetylene) and then cleaving the diester with HCl, with formation of alkyl chlorides. Here again, the alkylphosphonous esters used are prepared from the corresponding phosphonous dihalides by hydrolysis and reaction with alcohols.

The abovementioned reactions are very difficult to carry out, since their final step is cleavage of the corresponding esters, and this gives technical difficulties.

In addition, there are byproducts formed which, like some of the abovementioned starting materials, are toxic, or ignite spontaneously, and/or are corrosive, i.e. are highly undesirable.

SUMMARY OF THE INVENTION

The object on which the invention is based is therefore to provide a process which can prepare ethanebis(methylphosphinic) acid and is particularly easy and economic to carry out and gives high yield of a single product, and in particular dispenses with the complicated cleavage of diphosphinic esters. This process should also be clearly superior to the known processes in its effect on the environment.

This object is achieved by way of a process for preparing ethanebis(methylphosphinic) acids which comprises reacting ethyne (acetylene) with methylphosphinic acid:

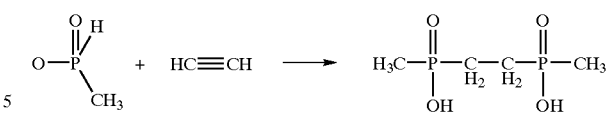

Compared with the processes known hitherto, the process of the invention has considerable advantages since it produces no halogenated organic byproducts, involves no complicated cleavage of phosphinic esters, and also has a positive balance in relation to product distribution. The process is highly effective and economic to carry out.

DETAILED DESCRIPTION OF THE INVENTION

Methylphosphinic acid is prepared in a simple and known manner by hydrolyzing methylphosphonous dichloride.

The methylphosphinic acid is preferably reacted with ethyne(acetylene) in the presence of a free-radical initiator.

The free-radical initiators used preferably comprise azo compounds.

The azo compounds are preferably cationic and/or non-cationic azo compounds.

The cationic azo compounds used preferably comprise 2,2'-azobis(2-amidinopropane) dihydrochloride or 2,2'-azobis(N,N'-dimethyleneisobutyramidine) dihydrochloride.

The non-cationic azo compounds used preferably comprise azobis(isobutyronitrile), 4,4'-azobis(4-cyanopentanoic acid), or 2,2'-azobis(2-methylbutyronitrile).

The free-radical initiators used preferably comprise peroxidic inorganic and/or peroxidic organic free-radical initiators.

The peroxidic inorganic free-radical initiators used preferably comprise hydrogen peroxide, ammonium peroxodisulfate, and/or potassium peroxodisulfate.

The peroxidic organic free-radical initiators used preferably comprise dibenzoyl peroxide, di-tert-butyl peroxide, and/or peracetic acid.

A wide selection of suitable free-radical initiators can be found by way of example in Houben-Weyl, Supplementary volume 20, in the chapter "Polymerisation durch radikalische Initiierung" [Free-radical-initiated polymerization] on pages 15–74.

The free-radical initiators are preferably metered in continuously during the reaction.

The free-radical initiators metered in continuously during the reaction are preferably in the form of a solution in the ethyne(acetylene).

The free-radical initiators metered in continuously during the reaction are preferably in the form of a solution in the solvent used.

The reaction preferably takes place at a temperature of from 40 to 200° C.

The reaction particularly preferably takes place at a temperature of from 70 to 130° C.

The reaction preferably takes place in the presence of a solvent.

The reaction preferably takes place in acetic acid as solvent.

The reaction preferably takes place by introducing gaseous ethyne (acetylene) at atmospheric pressure.

The reaction preferably takes place at superatmospheric pressure.

The manner of conducting the process is preferably such that after partial conversion the precipitating ethanebis(methylphosphinic) acid is filtered off, and further acetylene is added after replacing the methylphosphinic acid consumed.

The present invention also provides a process in which pure methylphosphinic acid is reacted with ethyne (acetylene) in the presence of a cationic or non-cationic free-radical initiator or in the presence of a peroxidic free-radical initiator, to give ethanebis(methylphosphinic) acid.

The present invention also provides a process in which methylphosphinic acid is reacted with ethyne (acetylene) in the presence of a cationic or non-cationic free radical initiator or in the presence of a peroxidic free-radical initiator in acetic acid, to give ethanebis(methylphosphinic) acid, and this is continuously removed from the reaction mixture by a circulating filter system, and the methylphosphinic acid consumed is likewise continuously replaced by fresh acid.

The desired ethane bis(methylphosphinic) acid is obtained with high selectivity and high purity.

Either the methylphosphinic acid or the ethyne (acetylene) may be used in excess, since the reaction partners always react In a molar ratio of 2 to 1 (methylphosphinic acid to ethyne (acetylene)).

The invention also provides the use of the ethanebis(methylphosphinic) acid prepared by the process of the invention as starting material for preparing flame retardants for polymers.

The invention further provides the use of the ethanebis(methylphosphinic) acid prepared by the process of the invention as starting material for preparing flame retardants for thermoplastic polymers, such as polyethylene terephthalate, polybutylene terephthalate, or polyamide.

The invention also provides the use of the ethanebis(methylphosphinic) acid prepared by the process of the invention as starting material for preparing flame retardants for thermoset resins, such as unsaturated polyester resins, epoxy resins, polyurethanes, or acrylates.

Finally, the invention also provides the use of the ethanebis(methylphosphinic) acid prepared by the process of the invention as precursor for the chemical synthesis of other phosphorus-containing compounds.

EXAMPLES

The examples below illustrate the invention:

Example 1

Ethanebis(methylphosphinic) Acid

A solution of 93 g of methylphosphinic acid in 200 g of glacial acetic acid is heated to about 90° C. in a 1l 5-necked flask equipped with gas inlet flit, thermometer, stirrer, reflux condensor, and initiator metering. A solution of 14 g (5 mol %) of ammonium peroxodisulfate in 30 g of water is metered in over a period of 5 h, with vigorous stirring. At the same time, about 10 l/h of ethyne (acetylene) are conducted through the solution by way of the gas inlet frit, excess acetylene being passed to a flare, The reaction temperature here is held at from about 95 to 105° C. Once the acetylene had been removed by flushing with nitrogen, the mixture was cooled, whereupon ethanebis(methylphosphinic) acid precipitates. This is filtered off, washed twice, each time with 50 ml of acetic acid, and dried at 100° C. under the vacuum provided by a water jet. This gives about 78 g of ethanebis(methyl-phosphinic) acid in the form of colorless crystals with a melting point of 197° C. (70% of theory, based on the [methylphosphonous] methylphosphinic acid used). The mother liquor comprises further final product (ethanebis(methylphosphinic) acid) and may be utilized for further reactions.

Elemental analysis: P: calc. 33.3%, found 33.0%; $^{31}$P NMR spectrum (D$_2$O): δ=55 ppm (singlet); purity ($^{31}$P NMR): 99%.

Example 2:

Ethanebis(methylphosphinic) acid

A solution of 160 g of methylphosphinic acid into 200 g of glacial acetic acid is heated to about 90° C. in a 1l 5-neck flask equipped with gas inlet frit, thermometer, stirrer, reflux condensor and initiator metering. A solution of 19 g (5 mol %) of 2,2'-azobis(2-methylbutyronitrile) in 100 g of glacial acetic acid is metered in over a period of 6 h, with vigorous stirring. At the same time, about 15 l/h ethyne(acetylene) are conducted through the solution by way of the gas inlet frit, excess acetylene being passed to a flare. The reaction temperature here is held at from about 95–105° C. Once the acetylene had been removed by flushing with nitrogen, the mixture is cooled, whereupon ethanebis(methylphosphinic) acid precipitates. This is filtered off, washed twice, each time with 50 ml of acetic acid, and dried out 100° C. under the vacuum provided by a water jet. This gives about 136 g of ethanebis(methylphosphinic) acid in the form of colorless crystals with a melting point of 199° C. and purity (31P-NMR) of 99% (73% of theory, based on the amount of methylphosphinic acid used). The mother liquor comprises further final product (ethanebis(methylphosphinic) acid) and may be utilized for further reactions.

What is claimed is:

1. A process for preparing ethanbis(methylphosphinic) acid, comprising the step of reacting ethyne (acetylene) with methylphosphinic acid, in the presence of acetic acid as solvent.

2. The process as claimed in claim 1, wherein at least one free-radical initiator is present during the reaction.

3. The process as claimed in claim 2, wherein the at least one free-radical initiator is an azo compound.

4. The process as claimed in claim 3, wherein the azo compound is selected from the group consisting of cationic and non-cationic azo compounds.

5. The process as claimed in claim 4, wherein the cationic azo compound is selected from the group consisting of 2,2'-azobis(2-amidinopropane) dihydrochloride and 2,2'-azobis(N,N'-dimethyleneisobutyramidine) dihydrochloride, and the non-cationic are compound is selected from the group consisting of azobis(isobutyronitrile), 4,4'-azobis(4-cyanopentanoic acid), 2,2'-azobis(2-methylbutyronitrile).

6. The process as claimed in claim 2, wherein the at least one free-radical is selected from the group consisting of peroxidic inorganic and peroxidic organic free-radical initiators.

7. The process as claimed in claim 6, wherein the peroxidic inorganic free-radical initiators are selected from the group consisting of hydrogen peroxide, ammonium peroxodisulfate, and/or potassium peroxodisulfate, and the peroxidic organic free-radical initiators are selected from the group consisting of dibenzoyl peroxide, di-tert-butyl peroxide, and peracetic acid.

8. The process as claimed in claim 2, wherein the at least one free-radical initiator is metered in continuously during the reaction.

9. The process as claimed in claim 8, wherein the at least one free-radical initiator metered in continuously during the reaction is in the form of a solution in the ethyne (acetylene).

10. The process as claimed in claim 8, wherein the at least one free radical initiator is metered in continuously during the reaction in the form of a solution in the acetic acid solvent.

11. The process as claimed in claim 1, wherein the reaction takes place at a temperature of from 40 to 200° C.

12. The process as claimed in claim 1, wherein the reaction takes place by introducing gaseous ethyne (acetylene) at atmospheric pressure.

13. The process as claimed in claim 1, wherein the reaction takes place at superatmospheric pressure.

14. A process for preparing ethanebis(methylphosphinic) acid comprising the steps of reacting methylphosphinic acid with ethyne (acetylene) in the presence of acetic acid as solvent and in the presence of a cationic or non-cationic free-radical initiator or in the presence of a peroxidic free-radical initiator in acetic acid, to give ethanebis (methylphosphinic) acid, continuously removing the ethanebis(methylphosphinic) acid from the reaction mixture by a circulating filter system, and continuously replacing the methylphosphinic acid consumed by introducing additional methylphosphinic acid to the reaction mixture.

15. The process as claimed in claim 1, wherein the reaction takes place at a temperature of from 70 to 130° C.

\* \* \* \* \*